US009382513B2

(12) United States Patent
Pain et al.

(10) Patent No.: US 9,382,513 B2
(45) Date of Patent: *Jul. 5, 2016

(54) METHOD OF MAKING AN AVIAN CELL LINE

(75) Inventors: Bertrand Pain, Lyons (FR); Fabienne Guehenneux, Orvault (FR)

(73) Assignee: Valneva, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/717,096

(22) Filed: Mar. 3, 2010

(65) Prior Publication Data

US 2010/0221825 A1 Sep. 2, 2010
US 2012/0070893 A9 Mar. 22, 2012

Related U.S. Application Data

(63) Continuation of application No. 12/350,781, filed on Jan. 8, 2009, now abandoned, which is a continuation of application No. 10/625,847, filed as application No. PCT/FR03/00735 on Mar. 7, 2003, now abandoned.

(30) Foreign Application Priority Data

Mar. 8, 2002 (FR) ..................................... 02 02945

(51) Int. Cl.
C12N 5/00 (2006.01)
C12N 5/0735 (2010.01)

(52) U.S. Cl.
CPC .......... *C12N 5/0606* (2013.01); *C12N 2500/90* (2013.01); *C12N 2500/92* (2013.01); *C12N 2500/95* (2013.01); *C12N 2510/02* (2013.01)

(58) Field of Classification Search
USPC .......................................... 435/325, 455, 377
See application file for complete search history.

(56) References Cited

U.S. PATENT DOCUMENTS

| 5,162,215 | A | 11/1992 | Bosselman |
| 5,340,740 | A | 8/1994 | Petitte |
| 5,453,357 | A | 9/1995 | Hogan |
| 5,589,458 | A | 12/1996 | Jameson et al. |
| 5,656,479 | A | 8/1997 | Petitte |
| 5,830,510 | A | 11/1998 | Petitte et al. |
| 6,114,168 | A | 9/2000 | Samarut |
| 6,500,668 | B2 | 12/2002 | Samarut |
| 6,656,479 | B2 | 12/2003 | Brake et al. |
| 6,998,266 | B2* | 2/2006 | Samarut et al. ............... 435/406 |
| 7,432,101 | B2 | 10/2008 | Guehenneux et al. |
| 7,771,980 | B2 | 8/2010 | Guehenneux et al. |
| 8,148,132 | B2 | 4/2012 | Mehtali et al. |
| 2002/0192815 | A1 | 12/2002 | Samarut et al. |
| 2004/0058441 | A1 | 3/2004 | Pain |
| 2004/0077086 | A1 | 4/2004 | Reiter et al. |
| 2009/0239297 | A1 | 9/2009 | Pain et al. |
| 2010/0062489 | A1 | 3/2010 | Guehenneux et al. |
| 2010/0111999 | A1 | 5/2010 | Guehenneux et al. |
| 2010/0235937 | A1 | 9/2010 | Valarche et al. |
| 2011/0294209 | A1 | 12/2011 | Pain et al. |
| 2012/0238001 | A1 | 9/2012 | Mehtali et al. |
| 2014/0154741 | A1 | 6/2014 | Guehenneux et al. |

FOREIGN PATENT DOCUMENTS

| CN | 1826406 | | 8/2006 |
| EP | 1 149 899 | A1 | 10/2001 |
| EP | 0 787 180 | B1 | 9/2002 |
| JP | 5-227947 | A | 9/1993 |
| WO | WO 90/01541 | | 2/1990 |
| WO | WO 93/15185 | | 8/1993 |
| WO | WO 93/23528 | | 11/1993 |
| WO | WO 94/03585 | | 2/1994 |
| WO | WO 96/12793 | A1 | 5/1996 |
| WO | WO 98/15614 | A1 | 4/1998 |
| WO | WO 99/06533 | A1 | 2/1999 |
| WO | WO 99/06534 | A1 | 2/1999 |
| WO | WO 00/03000 | A2 | 1/2000 |
| WO | WO 00/47717 | A1 | 8/2000 |
| WO | WO 01/26294 | A1 | 4/2001 |
| WO | WO 03/076601 | A1 | 9/2003 |
| WO | WO 2005/007840 | A1 | 1/2005 |
| WO | WO 2006/108846 | A1 | 10/2006 |
| WO | WO 2007/135133 | A1 | 11/2007 |
| WO | WO 2008/129058 | A1 | 10/2008 |

OTHER PUBLICATIONS

Pettite, Mech Dev. 121(9):1159-68. 2004, see pp. 1161-1162.*
Pain, Development. 1996, 122(8):2339-48.*
Horiuchi, J Biol Chem. 279(23):24514-20, 2004.*
table of Bird Classification/Families of the Eastern US Birds, 2009.*
Trentin (PNAS, Mar. 30, 2004, vol. 101, No. 13, pp. 4495-4500).*
Smith et al., "Buffalo Rat Liver Cells Produce a Diffusible Activity Which Inhibits the Differentiation of Murine Embryonal Carcinoma and Embryonic Stem Cells, Medline Abstract No. 87191399," *Dev. Biol.*, May 1987, pp. 1-9, vol. 12, No. 1, Academic Press, Orlando, FL.
Slager et al., "Transforming Growth Factor-Beta in the Early Mouse Embryo: Implications for the Regulation of Muscle Formation and Implantation, Medline Abstract No. 93365092," *Dev. Genet.*, 1993, pp. 212-224, vol. 14, No. 3, Wiley-Liss, Inc., New York.
Terstappen et al., "Analysis of Bone Marrow Stem Cell," *Blood Cells*, 1994, pp. 45-64, vol. 20, No. 1, Springer Verlag, New York, New York.
Seamark, "Progress and Emerging Problems in Livestock Transgenesis: A Summary Perspective," *Reprod. Fertil. Dev.*, 1994, pp. 653-657, vol. 6, CSIRO Publishing, Victoria, Australia.

(Continued)

Primary Examiner — Michael Wilson
(74) Attorney, Agent, or Firm — Wolf, Greenfield & Sacks, P.C.

(57) ABSTRACT

The present invention relates to a method for producing avian cell lines, comprising gradual or complete withdrawal of growth factors, serum and/or feeder layer so that the established lines are adherent or nonadherent cells capable of proliferating indefinitely in a basic culture medium. The invention also relates to the cells derived from such lines which are particularly useful for the production of substances of interest.

10 Claims, 5 Drawing Sheets

(56) References Cited

OTHER PUBLICATIONS

Figure 1:
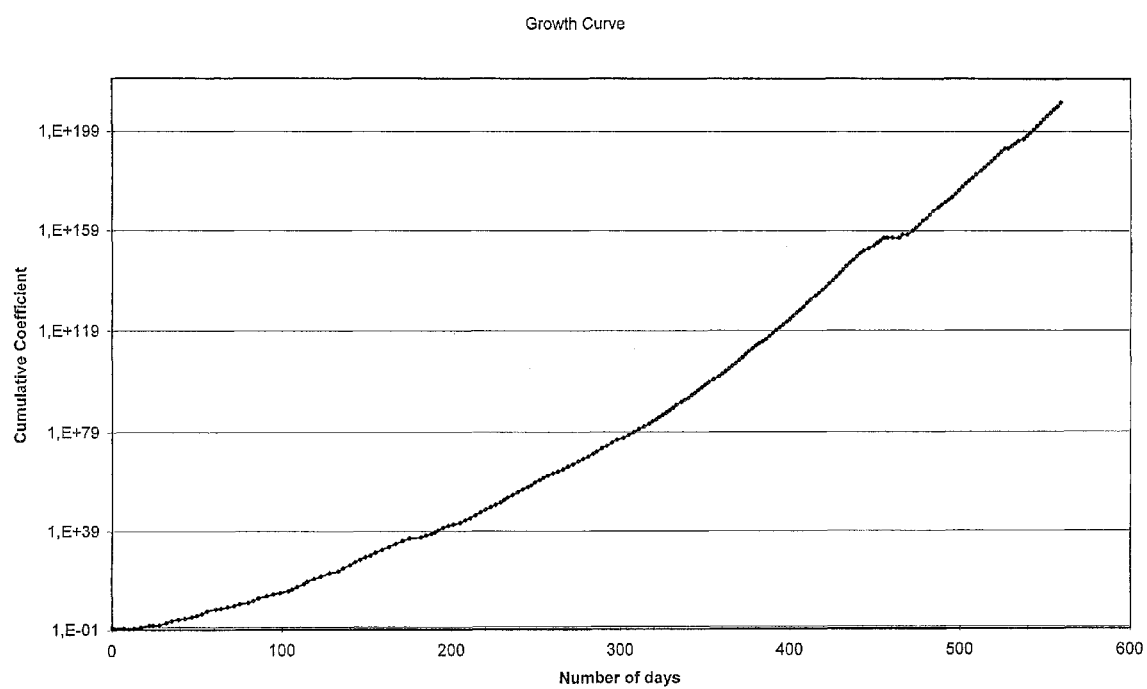

Mullins et al., "Perspectives Series: Molecular Medicine in Genetically Engineered Animals," *J. Clin. Invest.*, 1996, pp. S37-S40, vol. 98, The American Society for Clinical Investigation, Ann Arbor, MI.
Pain et al., "Long-Term in Vitro Culture and Characterization of Avian Embryonic Stem Cells with Multiple Morphogenetic Potentialities," *Development*, 1996, pp. 2339-2348, vol. 122, Company of Biologists Ltd., Cambridge, England.
Gibco Catalog, Gibco BRL, Gaithersburg, MD, 1992 and 1996, pp. 139, 152, 166, 172, 180, 195, and 198.
Chang et al., "Production of Germ Line Chimeric Chickens by Transfer of Cultured Primordial Germ Cells," *Cell Biology International*, 1997, pp. 495-499, vol. 21, Portland Press Ltd., London, England.
Hayman et al., "Self-Renewal and Differentiation of Normal Avian Erythroid Progenitor Cells: Regulatory Roles of the TGFα/c-ErbB and SCF/c-Kit Receptors," *Cell*, 1993, pp. 157-169, vol. 74, Cell Press, Cambridge, MA.
Bradley et al., Modifying the Mouse: Design and Desire, *Bio/Technology*, May 1992, pp. 534-539, vol. 10, Nature Publishing Company, New York, New York.
Simkiss, "Transgenic birds," Maclean, N. ed., Animals with Novel Genes, 1994, pp. 106-137, Cambridge University Press, Cambridge, England and New York, New York.
Chang et al., "Germ Line Chimera Produces by Transfer of Cultured Chick Primordial Germ Cells," *Cell Biol. Intern.*, 1995, pp. 569-576, vol. 19, No. 7, Elsevier, Amsterdam, Holland.
Godin et al., "Effects of the Steel Gene Product on Mouse Primordial Germ Cells in Culture," *Nature*, Aug. 29, 1991, pp. 807-809, vol. 352, Nature Publishing Group, London, England.
Galli et al., "Embryonic Stem Cells in Farm Animals," *Zygote*, Nov. 2, 1994, pp. 385-389, Cambridge University Press, Cambridge, England.
Soodeen-Karamath et al., "Apparent Absence of cot 3/4 From the Chick Genome, PUBMED Abstract PMID: 11139225," *Mol. Reprod. Dev.*, Feb. 2001, pp. 137-148, vol. 58, No. 2, Wiley-Liss, Inc., New York, New York.
Gardner et al., "Reflections on the Biology of Embryonic Stem (ES) Cells," *Int. J. Dev. Biol.*, 1997, pp. 235-243, vol. 41, UBC Press, Vancouver, B.C.
Zhou et al., "Production of a Hybridoma Cell Line Secreting Retinoic Acid-Specific Monoclonal Antibody," *J. Immunol. Methods*, Apr. 25, 1991, pp. 211-223, vol. 138, Elsevier, Amsterdam, Holland.
Twal et al., *Dev. Biol.*, Apr. 13, 1995, pp. 225-234, vol. 168, Elsevier, Amsterdam, Holland.
Sang, "Transgenic Chickens—Method and Potential Applications," *Trends Biotechnol.*, 1994, pp. 415-420, vol. 12, Elsevier, Amsterdam, Holland.
Etches et al., "Manipulation of blastodermal cells," *Poult. Sci.*, 1997, pp. 415-420, vol. 76, Poultry Science Association, Champaign, IL.
Petitte et al., "Production of Somatic and Germ Line Chimeras in the Chicken by Transfer of Early Blastodermal Cells," *Development*, 1990, pp. 185-189, vol. 108, Company of Biologists, Ltd., Cambridge, England.
Tajima et al., "Production of Germ Line Chimera by Transfer of Primordial Germ Cells in the Domestic Chicken (*Gallus Domesticus*)," *Theriogenology*, Sep. 1993, pp. 509-519, vol. 40, No. 3, Elsevier, Amsterdam, Holland.
Wall, "Transgenic Livestock: Progress and Prospects for the Future," *Theriogenology*, Jan. 1, 1996, pp. 57-68, vol. 45, No. 1, Elsevier, Amsterdam, Holland.
Pettie et al., "Avian Luripotent Stem Cells," *Mech. Dev.*, 2004, pp. 1159-1168, vol. 121, Elsevier, Amsterdam, Holland.
Horiuchi et al., "Chicken Leukemia Inhibitory Factor Maintains Chicken Embryonic Stem Cells in the Undifferentiated State," *J. Biol. Chem.*, Jun. 4, 2004, pp. 24514-24520, vol. 279, No. 23, The American Society for Biochemistry and Molecular Biology, Inc., Bethesda, MD.
Crocker et al., "Isolation and Characterization of Resident Stromal Macrophages and Hematopoietic Cell Clusters From Mouse Bone Marrow," *J. Exp. Med.*, Sep. 1985, pp. 993-1014, vol. 162, The Rockefeller University Press, New York, New York.
Ettenberg et al., "Cbl-b Inhibits Epidermal Growth Factor Receptor Signaling," Oncogene, 1999, pp. 1855-1866, vol. 18, *Stockton Press*, New York, New York.
Fayette et al., "Human Dendritic Cells Skew Isotype Switching of CD40-activated Naive B Cells Towards $IgA_1$ and $IgA_2$," *J. Exp. Med.*, Jun. 2, 1997, pp. 1909-1918, vol. 185, No. 11, The Rockefeller University Press, New York, New York.
Ferlin-Bezombes et a., "IFN-α Is a Survival Factor for Human Myeloma Cells and Reduces Dexamethasone-Induced Apoptosis[1]," *The Journal of Immunology*, 1998, pp. 2692-2699, vol. 161, The American Association of Immunologists, Bethesda, Maryland.
De Paulsen et al., "Role of Transforming Growth Factor-α in Von Hippel-Lindau $(VHL)^{-/-}$ Clear Cell Renal Carcinoma Cell Proliferation: A Possible Mechanism Coupling VHL Tumor Suppressor Inactivation and Tumorigenesis," *PNAS*, Feb. 13, 2001, pp. 1387-1392, vol. 98, No. 4, National Academy of Sciences, Washington, D.C.
I Drexler et al., *Highly attenuated modified vaccinia virus Ankara replicates in baby hamster kidney cells, a potential host for virus propagation, but not in various human transformed and primary cells*, 79 Journal of General Virology 347-352 (1998).
Acloque et al., Identification of a new gene family specifically expressed in chicken embryonic stem cells and early embryo. Mech Dev. May 2001;103(1-2):79-91.
Bosselman et al., Transmission of exogenous genes into the chicken. J Reprod Fertil Suppl. 1990;41:183-95.
Carsience et al., Germline chimeric chickens from dispersed donor blastodermal cells and compromised recipient embryos. Development. Feb. 1993;117(2):669-75.
Chang et al., Proliferation of chick primordial germ cells cultured on stroma cells from the germinal ridge. Cell Biol Int. Feb. 1995;19(2):143-9.
Chang et al., Simple method for isolation of primordial germ cells from chick embryos. Cell Biol Int Rep. Sep. 1992;16(9):853-7.
Chino et al., Skin reaction to yellow fever vaccine after immunization with rabies vaccine of chick embryo cell culture origin. Jpn J Infect Dis. Apr. 1999;52(2):42-4.
Dunwiddie et al., Presence of retrovirus reverse transcriptase-related gene sequences in avian cells lacking endogenous avian leukosis viruses. Proc Natl Acad Sci U S A. Aug. 1985;82(15):5097-101.
Enami et al., High-efficiency formation of influenza virus transfectants. J Virol. May 1991;65(5):2711-3.
Enami et al., Introduction of site-specific mutations into the genome of influenza virus. Proc Natl Acad Sci U S A. May 1990;87(10):3802-5.
Etches et al., Contributions to somatic and germline lineages of chicken blastodermal cells maintained in culture. Mol Reprod Dev. Nov. 1996;45(3):291-8.
Eyal-Giladi et al., From cleavage to primitive streak formation: a complementary normal table and a new look at the first stages of the development of the chick. I. General morphology. Dev Biol. Apr. 1976;49(2):321-37.
Forster et al., Tetracycline-inducible expression systems with reduced basal activity in mammalian cells. Nucleic Acids Res. Jan. 15, 1999;27(2):708-10.
Gerner et al., Heat-inducible vectors for use in gene therapy. Int J Hyperthermia. Mar.-Apr. 2000;16(2):171-81.
Gey et al., Long-term growth of chicken fibroblasts on a collagen substrate. Exp Cell Res. Mar. 15, 1974;84(1):63-71.
Ginsburg et al., Primordial germ cells of the young chick blastoderm originate from the central zone of the area pellucida irrespective of the embryo-forming process. Development. Oct. 1987;101(2):209-19.
Hagihara et al., Long-term functional assessment of encapsulated cells transfected with Tet-On system. Cell Transplant. Jul.-Aug. 1999;8(4):431-4.
Hahnel et al., The distribution of two cell surface determinants of mouse embryonal carcinoma and early embryonic cells. J Reprod Immunol. Feb. 1987;10(2):89-110.
Halloran et al., Laser-induced gene expression in specific cells of transgenic zebrafish. Development. May 2000;127(9):1953-60.

(56) References Cited

OTHER PUBLICATIONS

Hamburger et al., A series of normal stages in the development of the chick embryo. J Morph. 1951;88:49-92.
Huang et al., Expression of green fluorescent protein in oligodendrocytes in a time- and level-controllable fashion with a tetracycline-regulated system. Mol Med. Feb. 1999;5(2):129-37.
Hussain et al., Identification and characterization of avian retroviruses in chicken embryo-derived yellow fever vaccines: investigation of transmission to vaccine recipients. J Virol. Jan. 2003;77(2):1105-11.
Johnson et al., Characterization of endogenous avian leukosis viruses in chicken embryonic fibroblast substrates used in production of measles and mumps vaccines. J Virol. Apr. 2001;75(8):3605-12.
Kaaden et al., Establishment and characterization of chicken embryo fibroblast clone LSCC-H32. In Vitro. Oct. 1982;18(10):827-34.
Karagenç et al., Origin of primordial germ cells in the prestreak chick embryo. Dev Genet. 1996;19(4):290-301.
Karagenç et al., Soluble factors and the emergence of chick primordial germ cells in vitro. Poult Sci. Jan. 2000;79(1):80-5.
Kawase et al., Strain difference in establishment of mouse embryonic stem (ES) cell lines. Int J Dev Biol. Jun. 1994;38(2):385-90.
Kemble et al., Novel generations of influenza vaccines. Vaccine. May 1, 2003;21(16):1789-95.
Kemler et al., Reactivity of monoclonal antibodies against intermediate filament proteins during embryonic development. J Embryol Exp Morphol. Aug. 1981;64:45-60.
Kempe, Smallpox vaccination of eczema patients with attenuated live vaccinia virus. Yale J Biol Med. Aug. 1968;41(1):1-12.
Kingsley et al., Infectious laryngotracheitis virus, an alpha herpesvirus that does not interact with cell surface heparan sulfate. Virology. Apr. 10, 1999;256(2):213-9.
Kyhse-Andersen, Electroblotting of multiple gels: a simple apparatus without buffer tank for rapid transfer of proteins from polyacrylamide to nitrocellulose. J Biochem Biophys Methods. Dec. 1984;10(3-4):203-9.
Laemmli, Cleavage of structural proteins during the assembly of the head of bacteriophage T4. Nature. Aug. 15, 1970;227(5259):680-5.
Linial, A line of ring-necked pheasant cells susceptible to infection by avian oncornaviruses. Virology. Sep. 1976;73(2):548-52.
Liu et al., Lac/Tet dual-inducible system functions in mammalian cell lines. Biotechniques. Apr. 1998;24(4):624-8, 630-2.
Lovatt et al., High throughput detection of retrovirus-associated reverse transcriptase using an improved fluorescent product enhanced reverse transcriptase assay and its comparison to conventional detection methods. J. Virol. Methods. 1999;82:185-200.
Love et al., Transgenic birds by DNA microinjection. Biotechnology (N Y). Jan. 1999;12(1):60-3.
Luytjes et al., Amplification, expression, and packaging of foreign gene by influenza virus. Cell. Dec. 22, 1989;59(6):1107-13.
Maruyama et al., The antigenicity of chicken embryo fibrosis cell passaged strains of Japanese encephalitis viruses. Journal of Infection and Chemotherapy, vol. 60, pp. 251-256 (1986).
Matsui et al., Derivation of pluripotential embryonic stem cells from murine primordial germ cells in culture. Cell. Sep. 4, 1992;70(5):841-7.
Naito et al., Production of germline chimeric chickens, with high transmission rate of donor-derived gametes, produced by transfer of primordial germ cells. Mol Reprod Dev. Oct. 1994;39(2):153-61.
Nazerian, An updated list of avian cell lines and transplantable tumours. Avian Pathol. 1987;16(3):527-44.
Nieuwkoop et al., The migration of the primordial germ cells. In: Primordial Germ Cells in the Chordates. London: Cambridge University Press, pp. 113-127 (1979).
Ogura et al., Establishment of two chick embryo fibroblastic cell lines. Gann. May 1984;75(5):410-4.

Petitte et al., The origin of the avian germ line and transgenesis in birds. Poult Sci. Aug. 1997;76(8):1084-92.
Piquet-Pellorce et al., Are LIF and related cytokines functionally equivalent? Exp Cell Res. Aug. 1994;213(2):340-7.
Rang et al., The tetracycline-responsive promoter contains functional interferon-inducible response elements. Nucleic Acids Res. Mar. 1, 2000;28(5):1120-5.
Reed et al., A simple method of estimating fifty percent endpoints. Am. J. Hyg. 1938; 27:493-497.
Resnick et al., Phylogenetic distribution of the novel avian endogenous provirus family Eav-0. J Virol. Oct. 1990;64(10):4640-53.
Sellier et al., Comparative staging of embryo development in chicken, turkey, duck, goose, guinea fowl, and Japanese quail assessed from five hours after fertilization through seventy-two hours of incubation. J. Appl. Poult. Res. 2006; 15:219-228.
Shafren et al., Pathogenesis of avian encephalomyelitis viruses. J Gen Virol. Nov. 1991;72 (Pt 11):2713-9.
Solter et al., Monoclonal antibody defining a stage-specific mouse embryonic antigen (SSEA-1). Proc Natl Acad Sci U S A. Nov. 1978;75(11):5565-9.
Sugimoto et al., Characteristics of an attenuated vaccinia virus strain, LC16m0, and its recombinant virus vaccines. Vaccine. Jun. 1994;12(8):675-81.
Tartaglia et al., NYVAC: a highly attenuated strain of vaccinia virus. Virology. May 1992;188(1):217-32.
Thoraval et al., Germline transmission of exogenous genes in chickens using helper-free ecotropic avian leukosis virus-based vectors. Transgenic Res. Nov. 1995;4(6):369-77.
Thoraval et al., Somatic and germline chicken chimeras obtained from brown and white Leghorns by transfer of early blastodermal cells. Poult Sci. Dec. 1994;73(12):1897-905.
Tsang et al., Evidence of avian leukosis virus subgroup E and endogenous avian virus in measles and mumps vaccines derived from chicken cells: investigation of transmission to vaccine recipients. J Virol. Jul. 1999;73(7):5843-51.
Tsunekawa et al., Isolation of chicken vasa homolog gene and tracing the origin of primordial germ cells. Development. Jun. 2000;127(12):2741-50.
Uchida et al., Rapid and sustained hematopoietic recovery in lethally irradiated mice transplanted with purified Thy-1.1$^{lo}$ Lin- Sca-1+ hematopoietic stem cells. Blood. Jun. 15, 1994;83(12):3758-79.
Van De Lavoir et al., Germline transmission of genetically modified primordial germ cells. Nature. Jun. 8, 2006;441(7094):766-9.
Van De Lavoir et al., High-grade transgenic somatic chimeras from chicken embryonic stem cells. Mech Dev. Jan. 2006;123(1):31-41. Epub Dec. 1, 2005.
Wang et al., Progress toward the culture and transformation of chicken blastodermal cells. Stem Cells. Jul. 2006;24(7):1638-45.
Weissmahr et al., Reverse transcriptase activity in chicken embryo fibroblast culture supernatants is associated with particles containing endogenous avian retrovirus EAV-0 RNA. J Virol. Apr. 1997;71(4):3005-12.
Wilkinson et al., Expression pattern of the mouse T gene and its role in mesoderm formation. Nature. Feb. 15, 1990;343(6259):657-9.
Wood et al., An improved single-radial-immunodiffusion technique for the assay of influenza haemagglutinin antigen: application for potency determinations of inactivated whole virus and subunit vaccines. J Biol Stand. 1977;5(3):237-47.
Yang et al., Use of avian cytokines in mammalian embryonic stem cell culture. Poult Sci. Jul. 1994;73(7):965-74.
Yasuda et al., A method to obtain avian germ-line chimaeras using isolated primordial germ cells. J Reprod Fertil. Nov. 1992;96(2):521-8.
Zhu et al., Production of human monoclonal antibody in eggs of chimeric chickens. Nat Biotechnol. Sep. 2005;23(9):1159-69. Epub Aug. 28, 2005.

\* cited by examiner

METHOD OF MAKING AN AVIAN CELL LINE

CROSS REFERENCE TO RELATED APPLICATIONS

This application is a continuation-in-part of U.S. Patent Application Serial No. 12/350,781, now abandoned, filed on Jan. 8, 2009, which is a continuation of U.S. Patent Application Serial No. 10/625,847, filed on Jul. 24, 2003, which is a nonprovisional application under 35 U.S.C. §111(a) of International Application No. PCT/FR03/00735, filed on Mar. 7, 2003, and which claims priority to FR 0202945, filed on Mar. 8, 2002, all of which are incorporated herein by reference.

The present invention relates to a method for producing avian cell lines, in particular avian stem cells, comprising progressive or total withdrawal of growth factors; serum and/or feeder layer. These spontaneously established lines are adherent or nonadherent cells capable of proliferating indefinitely in a basic culture medium. The invention also relates to the cells derived from such lines which are particularly useful for the production of vaccines and of substances of interest.

Stem cells are cells identified by their culture in vitro from an embryo, from part of an embryo or even from an adult tissue. The expression stem cell is understood to mean any pluripotent cell of embryonic or adult origin which has a capacity for self-renewal and is capable of giving specialized differentiated cells. In other words, any noncancerous cell capable of dividing indefinitely in culture and of giving a daughter cell having the same capacity for proliferation and differentiation as the mother cell from which it is derived. These isolated cells exhibit particular morphological and immunocytochemical characteristics. It is also possible to distinguish the notion of:

- embryonic stem cells (CES cells), stem cells which have the characteristic feature of being obtained from culturing parts or all of a very early embryo (blastula stage). These CES cells exhibit in vitro all the characteristics of a stem cell, and in vivo the unique capacity of contributing to the morphogenesis of an embryo and of participating in germline colonization when they are reimplanted in any manner whatsoever in a recipient embryo.
- somatic stem cells (SSC), cells which have all the characteristics of stem cells when they are cultured in vitro, but which, unlike CES cells, do not have the potential to colonize in vivo the gonads after infection into an embryo. They contribute solely to the morphogenesis of the somatic tissues in the embryo.

Unlike already differentiated primary cells, stem cells do not exhibit an easily identifiable characteristic state of morphological differentiation (fibroblasts, adipocytes, macrophage, and the like), but are rather characterized by a state of proliferation and of nondifferentiation. This state results different behaviors such as a rapid proliferation in vitro, a characteristic morphology, the presence of different markers, variable requirements for growth factors and an ability to respond to particular stimuli for induction of differentiation. They are not sensitive to replicative senescence, a critical period for a large number of differentiated primary cells, including the fibroblasts for example.

To maintain avian stem cells in vitro for long periods of time, it is necessary to observe specific culture and maintenance conditions as described in Pain et al., 1996; U.S. Pat. No. 6,114,168 and EP 787 180.

The in vitro culture of a primary cell under satisfactory medium and growth factor conditions allows it to proliferate only for a certain number of passages. This cell can be obtained directly from a dissociated tissue or from part of this tissue. This number of passages is nevertheless highly dependent on the animal species considered, on the origin of the tissue, on the age of the donor organism and the like.

In most cases, the cell proliferation observed in vitro slows progressively and then the cells stop proliferating.

This arrest often corresponds to a replicative senescence, known by the term Hayflick limit. This stoppage is thought to be the result of the action of a true molecular clock of which one of the key components is thought to be the length of the telomeres. The telomeres are repeat sequences situated at the end of the chromosomes. The shortening of these repetitive nucleotide structures is the consequence of the replication of DNA on a semiconservative mode. In the absence of the telomerase enzyme, which is in charge of adding the repeat sequences at the end of the chromosomes, a point of no-return is reached with regard to the size of the telomeres, a point beyond which an as yet unknown molecular mechanism for activation of genes involved in controlling the cell cycle is triggered. The cells are then thought to be blocked in the G1 phase in their divisions and are thought to stop proliferating. Numerous factors appear to be involved in this negative control of the cell cycle such as various cyclins, specific kinases, RB and P53 proteins, specific transcription factors such as E2F and many others (mdm2, BTG, p21, and the like). Conversely, the telomerase enzyme can therefore be viewed as a central factor in cell immortality because it maintains the length of the telomeres and therefore makes the cell insensitive to this loss caused by successive divisions.

In an organism under development and during the life of this organism, only a few cell types, including certain lymphocytes, exhibit a permanent expression of telomerase. This activity also appears to be one of the characteristics of stem cells, both at the somatic level (SSC) and at the germline level. This property of expressing, of maintaining of expression and of "awakening" expression of the telomerase activity is also often associated with the immortal character of a cell maintained in vitro. To date, numerous cancer cells are also detected positive for telomerase activity. This activity is thought to be partially responsible for the capacity for uncontrolled proliferation of tumor cells in vivo.

This telomerase activity is, in all cases, an excellent marker for the stem cell character and for the germline lineage and for the capacity of a cell to become immortal. Two criteria are therefore used: the telomerase activity and the size of the telomeres.

In an establishment perspective and very briefly, according to the literature and the results already available in many laboratories, the establishment of cell lines may be carried out according to two routes: a spontaneous establishment resulting from noninduced intrinsic genetic damage or a triggered establishment, induced by the use of viruses, retroviruses or by other means such as chemical agents, irradiation, UV (ultraviolet) radiation, and the like. In mammals, for example, the establishment of rodent (mouse, rat, and the like) cells is recognized as being fairly easy spontaneously; on the other hand, the situation is quite different for human cells regardless of their tissue origin (Smith and Pereira-Smith, 1996).

Thus, when it is desired to obtain cell lines from the above-mentioned avian stem cells so as to produce a mass of substances of interest in vitro, the problem is to be able to maintain cells in culture in an economical medium while avoiding stumbling blocks such as cellular differentiation and senescence.

At the avian level, it is generally accepted that the establishment of primary cells is a rare, or even practically nonexistent event. The only notable published exception appears to be the DF-1 line which results from the immortalization, described as being spontaneous, of chicken fibroblasts (Foster et al., 1991; U.S. Pat. No. 5,672,485, ATCC No. CRL 12203). At the level of this line, recent articles mention the first components of observed deregulation (Kim et al., 2001a; Kim et al., 2001b).

In the immortalization process, a first step leads the proliferating cell to the Hayflick limit which, depending on the cell types, is between 10 and 50 passages. A first spontaneous mutational event then takes place which allows the cell to cross this first blockage, an event which often affects the p53 and pRb genes, and the like. The cells therefore continue to proliferate until the moment when a second blockage occurs, which is in general lifted by new mutations in other genes and by the activation of telomerase, which is often observed.

At the avian level, it is in general accepted that the establishment of immortal primary cells is a practically nonexistent event. Accordingly, a large number of lines have been obtained by culturing tumor cells, often directly taken from a biopsy of the tumor. This obtaining in vitro is in fact the result of the impairment in vivo of certain genes, which are responsible for the appearance of the tumor. An example is provided by the fibroblast line SB-CEV-1, which is isolated from the culturing of a visceral tumor from an animal (ATCC No. CRL 10497, U.S. Pat. No. 5,846,527). This approach is greatly facilitated by the existence of a very large number of avian viruses and retroviruses which have been identified, isolated and often characterized at the molecular level. Being often oncogenic by their direct or indirect action (activation of a transforming endogenous gene during their integration, expression of the oncogenic protein(s) endogenous to the virus), these viruses cause tumors and lesions; thus, the obtaining of cell lines in different differentiated lineages is possible from the culturing of the infected organs of the animals. The in vitro use of these viruses and retroviruses, isolated in vivo, has been developed in addition. There may thus be mentioned nonexhaustively:

- the lymphoblastoid lines DT40 and DT95, obtained in the presence of the avian leukosis virus (ALV) and in which the myc locus is activated (Baba et al., 1985, ATCC No. CRL 2111, CRL 2112),
- the turkey lymphoblastoid line MDTC-RP19, established with the Marek's disease virus (U.S. Pat. No. 4,388,298, ATCC No. 8135),
- the lymphoblastoid line ConA-C1, established with the REV virus (reticuloendothelial virus, ATCC No. 12135, U.S. Pat. No. 5,691,200),
- the myelomonocytic line BM2 established with the MH2 virus (Liu et al., 1977, U.S. Pat. No. 5,388,680),
- and a whole series of hematopoietic lines obtained with different viruses,
  - the erythroblastic line HD4 (6C2), obtained with the AEV virus
  - the monocytic line HD11 (Beug et al., 1979), obtained with the MC29 virus
  - the granulocytic line HD13 (Golay et al., 1988), obtained with the E26 virus
  - the mixed hematopoietic line HD57 (Metz and Graf, 1991) also obtained with the E26 virus.

However, the problem in these transformation approaches is the obtaining of cells which produce viruses and carry the activated genome of the viruses and retroviruses used. These activations and this viral presence are brakes on their industrial use as replication support for viruses of interest or for the production of specific proteins under optimum safety conditions.

Another approach to overexpression of oncogenes, of immortalizing genes (adenovirus E1A gene, polyoma SV40 "large T", and the like) or gene fragments has also made it possible to obtain lines from already differentiated primary cells. These components may be introduced into the cells by simple transfection of a vector allowing the expression of the immortalizing part, but may also be introduced via viruses or retroviruses which have been genetically modified to express these immortalizing components. The origin of the immortalizing components may be avian or otherwise, viral or otherwise. The tropism for avian cells can in fact be linked to the original virus or can also be modified. By way of example, the duck fibroblast line TDF-2A is thus obtained by introducing a first immortalizing gene and then an antiapoptotic gene (Guilhot et al., 1993, U.S. Pat. No. 6,255,108). Other methods have been developed, such as the overexpression of p53 (Foster et al., U.S. Pat. No. 5,830,723).

In addition, the action of chemical carcinogens directly on the animal according to different modes of administration has allowed, inter alia, the obtaining

- of the QT6 and QT35 lines, of quail fibroblasts (Moscovici et al., 1977, ATCC No. CRL 1708),
- of the chicken hepatocyte line LMH (Kawaguchi et al., 1989, ATTC No. CRL 2117),
- of the chicken fibroblast line CHCC-OU2 (ATCC No. CRL 12302, U.S. Pat. No. 5,989,805).

The expression immortalization event is understood to mean various actions such as:

- the action of oxidative, heat or chemical stress capable of inducing modifications in the physiology of the cells and/or mutations,
- the action of the products of specific genes in the physiology of the cells, such as certain immortalizing genes (oncogenes, protooncogenes, cell cycle genes, antiapoptotic genes and the like),
- targeted destruction by functional recombination or inactivation of antioncogenes, apoptotic genes, tumor suppressor genes, antiproliferative genes, leading to a functional deregulation of the cell cycle or of the physiology of the cell,
- the control of proliferation genes by their functional blocking, and the like,
- the action of rays (UV, gamma, X, and the like),
- the action of chemical mutagens (substances which damage DNA, substances similar to growth factors, and the like),
- the conjugated action of these various actions taken separately.

In the context of the invention, it has been found that the withdrawal of growth factors, serum and/or feeder layer leads to the isolation of populations of stem cells, in particular of somatic stem cells, which can grow indefinitely in basic culture media.

In addition, apart from the hematopoietic stem cells which are for the most part nonadherent cells, the majority of the cells, obtained according to the prior art techniques mentioned above (fibroblasts, hepatocytes, and the like), exhibit an adherent phenotype. Now, the industrial use of cells, as viral replication support, favors nonadherent cells. This phenotype is advantageous both because of ease of handling which avoids the use of a proteolytic enzyme for dissociation and for the high densities reached by nonadherent cells cultured in vitro.

The present invention describes the production of lines which can become spontaneously nonadherent and for which the nonadherence is obtained by a withdrawal of the feeder layer. Because of their growth in suspension, these lines are perfectly suitable for industrial use for the production of substances of interest in bioreactors.

In addition to their properties of growing on a basic culture medium, it has been discovered that these cell lines allow the replication of certain viruses in yields equivalent to or even higher than the yields obtained with current methods, which makes these cells particularly useful for the mass production of vaccines.

DESCRIPTION

Thus, in a first aspect, the present invention relates to a method for producing avian cell lines, characterized in that it comprises the following steps:

a) culturing avian cells in a medium containing all the factors allowing their growth and an inactivated feeder layer, b) passage by modifying the culture medium so as to obtain progressive or total withdrawal of said factors, of the serum and/or of the feeder layer, c) establishing adherent or nonadherent cell lines capable of proliferating in a basal medium in the absence of exogenous growth factors, serum and/or inactivated feeder layer.

In the context of the invention, the expression "establishment of a line" is understood to mean maintaining cells in culture in vitro over a considerable period of time. Advantageously, the cells derived from the lines obtained in step c) are capable of proliferating for at least 50 days, 100 days, 150 days, 300 days or preferably at least 600 days. The 600 days do not constitute a time limit because the cell lines obtained are still alive after much longer time periods. Hence, these lines are considered as being able to grow indefinitely in a basic culture medium free of exogenous growth factors, serum and/or inactivated feeder layer. The expression "line" is understood to mean any population of cells capable of proliferating indefinitely in culture in vitro while retaining to a greater or lesser degree the same morphological and phenotypic characteristics.

The cells derived from the lines according to the invention may be avian stem cells, in particular avian somatic stem cells.

The stem cells according to the invention can serve to obtain differentiated cell lines. Indeed, these stem cells have the property of being pluripotent, that is to say that they have the potential to be induced in multiple differentiation pathways which can be characterized by various specific markers.

These cells can also be precursor cells, which correspond to the partially differentiated cells of an adult or embryonic tissue, by contrast to a stem cell and which is capable of dividing and of giving more differentiated cells. The expression "differentiated cell" is understood to mean any specialized cell of an adult or embryonic tissue, having specific markers or fulfilling specific physiological functions. It is possible, in a particular aspect of the invention, in particular for particular isolates or clones derived from a particular isolate obtained during establishment, for these stem cells to contribute to the germline. In this case, these stem cells established as lines are thought to be embryonic stem cells.

Of course, the method mentioned above makes it possible to obtain cellular clones derived from cells obtained from established lines. These clones are cells which are genetically identical to the cell from which they are derived by division.

In a particular embodiment, the invention relates to a method as defined above, in which the established lines are adherent stem cells which proliferate in the absence of inactivated feeder layer.

In this regard, in the method described above, step b) consists in a withdrawal of the components of the medium (growth factors alone or serum alone or growth factors and then serum or alternatively serum and then growth factors). We also found that it is possible to obtain non adherent cells after several passages, at any moment, from these adherent stem cells that proliferate with or without feeder layer.

In another embodiment, the invention relates to a method as defined above in which the established lines are nonadherent stem cells which proliferate in suspension in a medium free of exogenous growth factors.

In this regard, in the method described above, step b) consists in a progressive or total withdrawal of the feeder layer and then optionally in a withdrawal of the other components of the medium (growth factors and serum).

In another embodiment, the invention relates to a method as described above in which the established lines are nonadherent stem cells which proliferate in suspension in a medium free of serum (serum-free medium).

In another embodiment, the invention relates to a method as defined above, in which the established lines are nonadherent stem cells which proliferate in suspension in a medium free of exogenous growth factors and serum.

In another alternative, step b) consists in a progressive or total withdrawal of the growth factors, optionally followed by a progressive withdrawal of the serum.

In another alternative, step b) consists in a progressive or total withdrawal of the growth factors and/or serum, optionally followed by a withdrawal of the feeder layer.

In addition, the established lines may be cells which proliferate in a serum-depleted medium, in particular in a medium free of serum. The expression serum-depleted is understood to mean a gradual reduction of the concentration of serum spread out over time. This method allows a selection of clones which adapt to these new, increasingly drastic conditions until stable lines are obtained which are capable of growing in a serum-depleted medium or in a medium completely free of serum.

The method described above may additionally comprise a step in which the cells obtained in step c) are subjected to a selection in culture media used for large-scale production so as to obtain clones suitable for the production of vaccines intended for human or animal therapy.

The cells according to the invention have at least one of the following characteristics:
 a high nucleocytoplasmic ratio,
 an endogenous alkaline phosphatase activity,
 an endogenous telomerase activity,
 a reactivity with specific antibodies selected from the group of antibodies SSEA-1 (TEC01), SSEA-3, and EMA-1.

Preferably, the cells of the invention have all the above-mentioned characteristics.

In an additional aspect, the invention relates to a method for producing avian lines, which is mentioned above, in which the cells derived from the lines obtained in step c) are modified in order to allow a better use in vitro such as the extension of the greater life span or growth densities or alternatively of the lower nutrient requirements.

Advantageously, the cells derived from established lines are modified in order to produce a substance of interest, in particular a polypeptide of interest, an antibody or an attenuated virus. Said cells may be modified by any technique accessible to persons skilled in the art, in particular homologous, directed and/or conditional recombination (Cre-Lox or FLP-FRT system), by transformation with any vector, plasmid, in particular with the aid of retroviruses.

The medium used in step a) may comprise at least one factor selected from cytokines, in particular LIF, IL-11, IL-6, IL-6R, CNTF, Oncostatin and other factors such as SCF, IGF-1 and bFGF.

In addition, the inactivated feeder layer used in step a) is preferably composed of fibroblasts, including mouse fibroblasts established as a line. Among these fibroblasts are in particular the STO cells which may or may not be modified or transfected with expression vectors (Pain et al., 1996). In this method, the cells used in step a) are cells obtained by suspending cells obtained from blastodermal disks of fertilized eggs in a culture medium comprising at least one cytokine, b-FGF, and SCF. Said cells are inoculated into a layer of feeder cells, incubated, and then collected.

Step b) consists in a progressive withdrawal of each growth factor added to the medium in step a), in particular a cytokine, b-FGF, and SCF, comprising a passage in a new medium free of at least one of said factors and in repeating various successive passages until the medium is free of all of said factors. The expression progressive withdrawal is understood to mean a removal factor by factor from the culture medium. Alternatively, it is possible to carry out a drastic or total withdrawal, that is to say the removal of all of said factors all at once. Thus, the withdrawal of step b) may consist in progressively reducing the concentration of one or more factors or in culturing the avian stem cells directly in a medium free of one or more factors or alternatively free of all of said factors.

Step b) may also comprise the withdrawal of the serum. In this regard, the withdrawal may be progressive, by reducing the serum concentration during each passage, for example on passing from 10% to 7.5% and then 3.75% and 2%, tending toward 0% (serum-free medium). Alternatively, a drastic withdrawal may be carried out.

Step b) may also comprise the withdrawal of the feeder layer. The withdrawal of the feeder layer may also be gradual, by reducing the number of inactivated feeder cells during each passage. Alternatively, it is possible to carry out a drastic withdrawal.

Of course, the order of withdrawals can vary. For example, it is possible to start with the withdrawal of the growth factors and continue with the withdrawal of the feeder layer.

Thus, in another aspect, the invention relates to the established cell lines and to the cells derived from said lines which can be obtained from the method described above, said cells being capable of proliferating for at least 50 days, 100 days, 150 days, 300 days, or preferably at least 600 days in a medium free of exogenous growth factor, serum and/or feeder layer.

These cell lines and the cells derived therefrom are capable of proliferating for at least 50 days, 100 days, 150 days, 300 days, or preferably at least 600 days in a basal medium, in particular in a medium such as DMEM, GMEM, HamF12 or McCoy supplemented with various additives commonly used by persons skilled in the art. Among the additives, there may be mentioned nonessential amino acids, vitamins and sodium pyruvate.

The invention also relates to the cell lines and the cells derived from such lines described above, characterized in that they are avian stem cells, in particular avian somatic stem cells or avian embryonic stem cells.

These stem cells may be adherent, while proliferating in the absence of the inactivated feeder layer. Alternatively, these stem cells are nonadherent and proliferate in suspension in a basal medium mentioned above.

These cells are also characterized in that they have at least one of the following characteristics:
  a high nucleocytoplasmic ratio,
  an endogenous alkaline phosphatase activity,
  an endogenous telomerase activity,
  a reactivity with specific antibodies selected from the group of antibodies SSEA-1 (TEC01), SSEA-3, and EMA-1.

Advantageously, these cells are genetically modified so as to produce a substance of interest, in particular a polypeptide of interest, an antibody or an attenuated virus.

Cells of the invention can for example support the replication of live or attenuated viruses, in particular the viruses selected from the group of adenoviruses, hepadnaviruses, herpesviruses, orthomyxoviruses, papovaviruses, paramyxoviruses, picornaviruses, poxviruses, reoviruses and retroviruses.

Preferably, the viruses belong to the family of orthomyxoviruses, in particular the influenza virus, to the family of paramyxoviruses, in particular the measles, mumps and rubella viruses.

In another embodiment, the viruses replicated on these cells belong to the to the family of poxvirus, in particular canarypox virus, fowlpox virus as well as vaccinia virus.

Thus, the invention relates to the cell lines described above, the cells derived from said lines and also the cell lines obtained from cells which have been genetically modified. Preferably, the invention relates to the cell lines derived from step c) of the method described above, characterized in that they are avian stem cells capable of growing indefinitely in a basal medium free of exogenous growth factors, depleted of serum or free of serum and/or of feeder layer.

In another aspect of the invention, the cells obtained at the end of step c) may be genetically modified.

The invention also relates to a cell culture comprising cells derived from the cell lines described above, in particular avian stem cells or avian embryonic stem cells, and a basal medium free of exogenous growth factors depleted of serum or free of serum and/or of inactivated feeder layer.

In an additional aspect, the invention relates to the use of the cell lines and cells described above for the production of substances of interest, in particular of proteins of therapeutic interest, for the replication of live or attenuated viruses, in particular viruses chosen from the group of adenoviruses, hepadnaviruses, herpesviruses, orthomyxoviruses, papovaviruses, paramyxoviruses, picornaviruses, poxviruses, reoviruses and retroviruses.

Preferably, the cell lines and the cells described above are used for the production of viruses belonging to the family of orthomyxoviruses, in particular the influenza virus, and for the production of viruses belonging to the family of paramyxoviruses, in particular the measles, mumps and rubella viruses.

It is possible to introduce into these lines and cells, used for supporting the replication of live or attenuated viruses, the component(s) necessary for accomplishing the complete viral cycle of the virus so as to obtain, for example, the overexpression of the receptor for the virus at the surface of the cell.

Therefore, one best mode of the invention is to use the cells as defined above to produce live or attenuated vaccine, for example recombinant vaccine, comprises culturing the adherent or non adherent cell lines established in step c) according to the process described above, inoculating said cells with viral particles and culturing said cells in a basal medium as mentioned above until cell lysis occurs and newly produced viral particles are released in said medium. The invention has shown to be particularly useful for the production of attenuated virus belonging to the family of poxvirus, in particular canarypoxvirus, fowlpoxvirus and vaccinia virus such as such as native or recombinant vaccinia virus (for example Modified Vaccinia virus Ankara, MVA (such as MVA available under ATCC Number VR-1508) or other orthopoxviruses) and is further described in the examples below.

Furthermore, the invention is aimed at the use of the cells according to the invention for producing recombinant viruses expressing antigens as vaccine against infection diseases such as smallpox and cancer (for example melanoma, prostate cancer, breast cancer, lung cancer, ovary cancer, liver cancer . . . ).

For the remainder of the description, reference will be made to the legend to the figures below.

LEGEND

Figure 2:
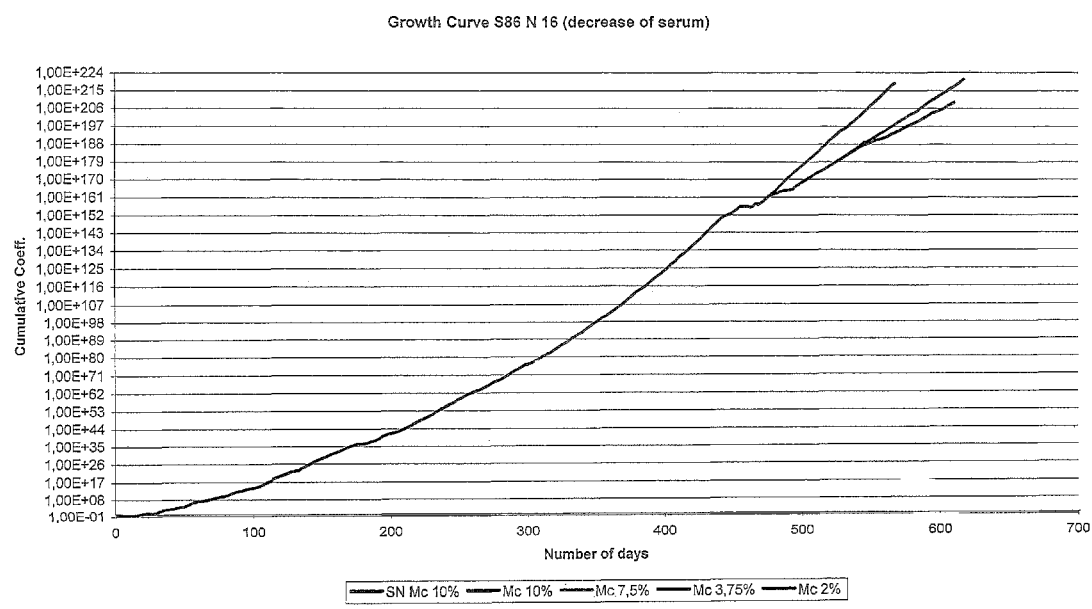
Figure 3:
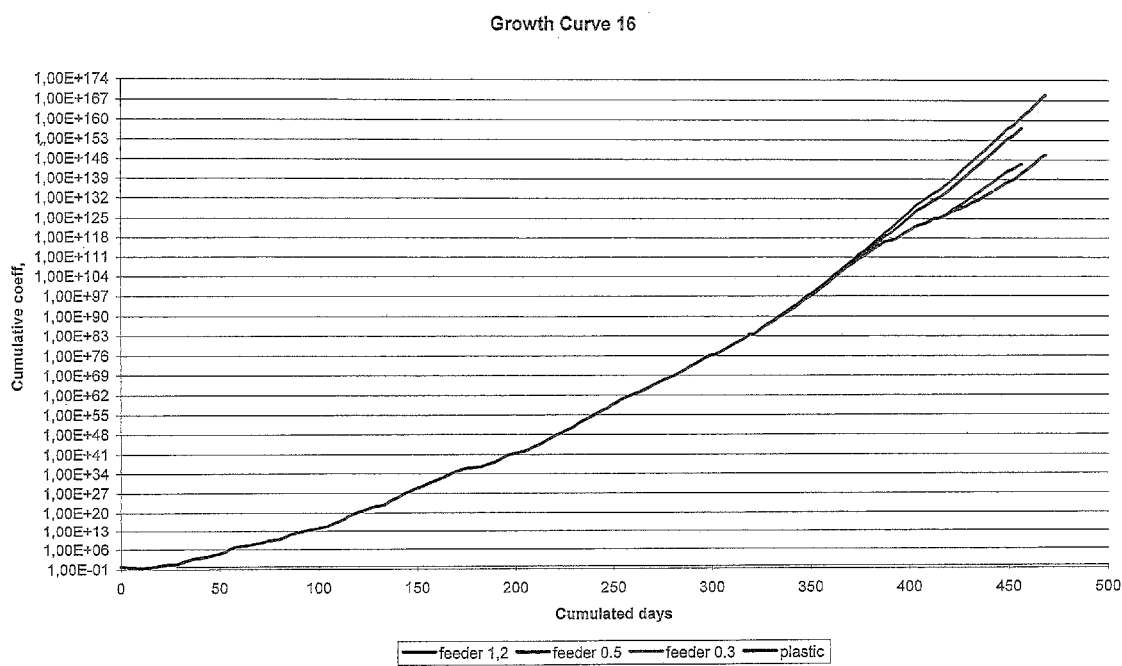

FIGS. 1-3: Growth curves for the cell lines of the invention (with withdrawal of serum (FIG. 2) and with withdrawal of feeder layer (FIG. 3).

Figure 4:
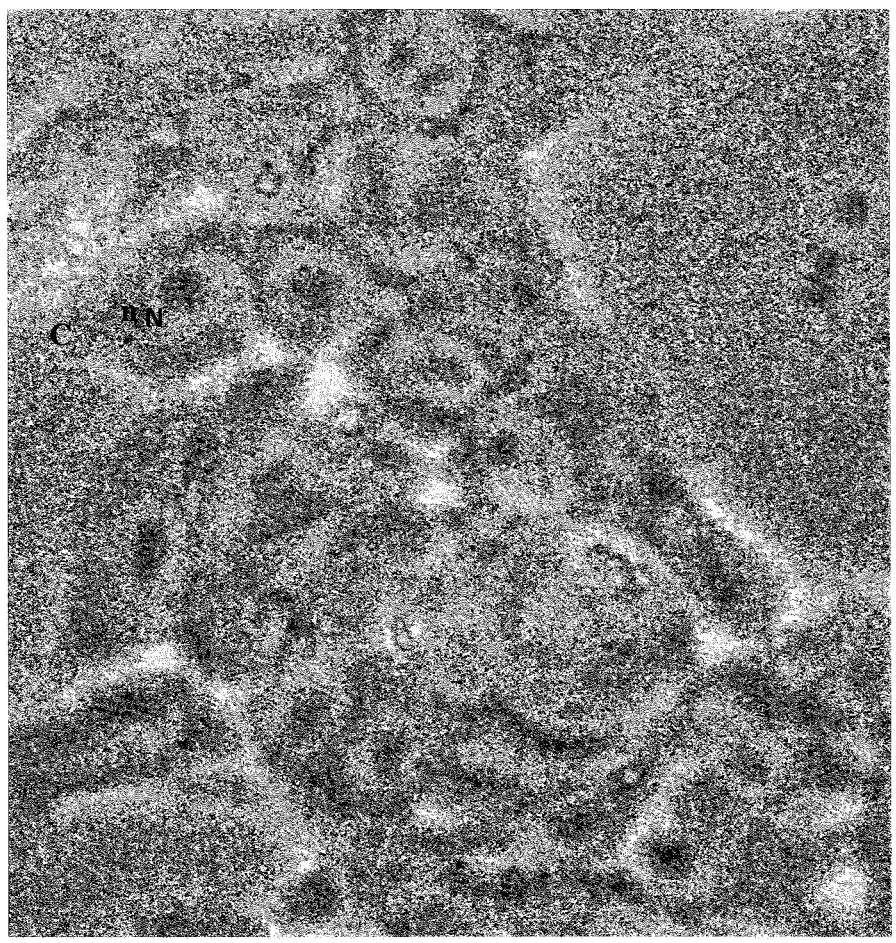

FIG. 4: Photograph, showing the characteristic morphology of avian stem cells N: nucleus, n: nucleolus and C: cytoplasm (isolate S86N99, ×40 magnification, photograph taken with a Sony Cyber-shot digital camera)

Figure 5A:
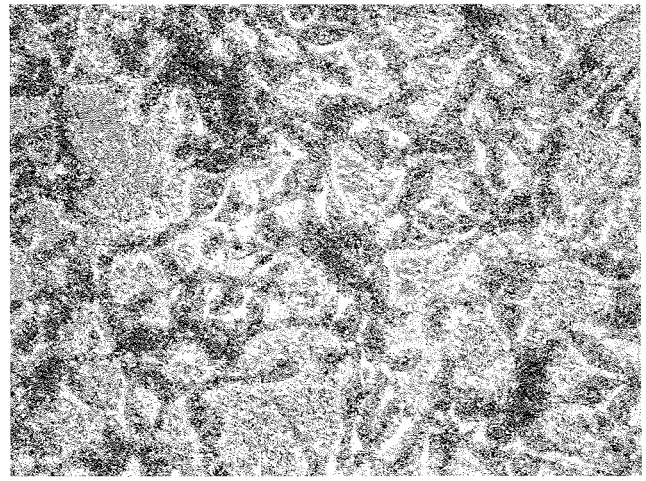
Figure 5B:
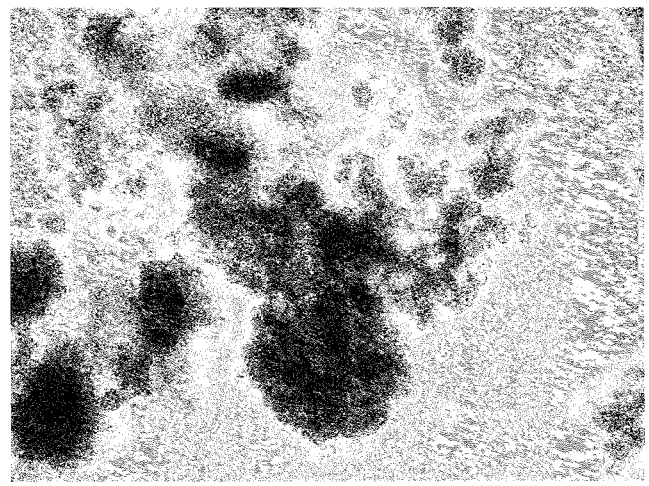

FIG. 5: Photograph showing the alkaline phosphatase activity of avian stem cell lines which are adherent or which are in suspension After fixing (0.1% formaldehyde/0.5% glutaraldehyde, 30 minutes at 4° C.), the cells are rinsed twice in 1×PBS and incubated for between 10 and 30 minutes at 37° C. in an NBT/BCIP (Nitro Blue Tetrazolium chloride 0.375 mg/ml, 5-bromo-4-chloro-3-indolyl phosphate 0.188 mg/ml, 0.1M Tris pH 9.5, 0.05M $MgCl^2$, 0.1M NaCl) solution. The reaction is stopped by two 1×PBS washes and the photographs are taken.

A—illustrates the characteristic violet coloration of the endogenous alkaline phosphatase activity obtained with the adherent line S86N45 p87, a line cultured with no feeder or factor (×40 magnification, Sony Cyber-shot digital camera).

B—illustrates the violet coloration characteristic of the endogenous alkaline phosphatase activity obtained with the EB14 line maintained from 8 passages in suspension, line derived from the S86N45 cells, cultured in suspension with no feeder or factor (×20 magnification, Sony Cyber-shot digital camera).

EXAMPLE 1

Variable Origin of the Live Material Used

The establishment of cell lines is often greatly linked to the genetic nature of the cell material. Thus, in the murine example, proportionately few genetic bases are permissive to the production of embryonic stem ES cells and often involves a notion of inbred animals. In the case of avian animals, it is difficult to obtain inbred animals for historical reasons and because of the origin of selection of commercial strains; it being of interest precisely to avoid inbreeding. Eggs are the initial source of the cells cultured in this invention. The eggs are preferably used nonincubated, but a few hours of incubation may be necessary in order to obtain the first stages of development of the embryo. The cells obtained are derived from different chicken strains. Among the strains used, there may be mentioned the S86N strain, a commercial strain intended for the production of chicken bearing a quality label, CNRs, the strain intended for the production of chicken bearing a quality label, Marens, a local strain which is genetically and phenotypically well characterized, White Leghorns, a strain more intended for the production of eggs for consumption and a reference strain for research laboratories, and the like. In the latter strain, various origins have been tested including certain eggs (called Valo) obtained from the White Leghorn strain from Lohmann (Germany) considered to be "SPF" (Specific Pathogen Free) eggs kept under very particular health safety conditions. Numerous cell isolates were obtained from various strains, suggesting the general character of the method.

EXAMPLE 2

Production and Establishment of the Adherent Cells

The eggs are opened, the yolk is separated from the egg white during the opening. The embryos are removed from the yolk either directly or with the aid of a Pasteur pipette, or with the aid of a small absorbent filter paper (Whatmann 3M paper), cut out beforehand in the form of a perforated ring with the aid of a punch. The diameter of the perforation is about 5 mm. These small rings are sterilized using dry heat for about 30 minutes in an oven. This small paper ring is deposited on the surface of the yolk and centered on the embryo which is thus surrounded by the paper ring. The latter is then cut out with the aid of small pairs of scissors and the whole removed is placed in a Petri dish, filled with PBS or with a physiological saline. The embryo thus carried away by the ring is cleaned of the excess yolk in the medium and the embryonic disk, thus freed of the excess vitellin, is collected with a Pasteur pipette.

In both cases, the embryos are placed in a tube containing physiological medium (1×PBS, Tris Glucose, medium, and the like). The embryos are then mechanically dissociated and inoculated on a "feeder" into defined culture medium. Among the preferred conditions used for the culturing, preference is given to the culture medium composed of MacCoy medium as basal medium supplemented with fetal calf serum at an initial concentration of 12 to 8%, with nonessential amino acids at 1%, with a mixture of vitamins of commercial origin at 1%, with sodium pyruvate at a final concentration of 1 mM, with beta-mercaptoethanol at a final concentration of 0.2 mM, glutamine at a final concentration of 2.9 mM, with an initial mixture of antibiotics containing gentamycin at a final concentration of 10 ng/ml, penicillin at a final concentration of 100 U/ml and streptomycin at a final concentration of 100 µg/ml. Rapidly after the first passages of the cells, the mixture of antibiotics is no longer added to the medium. The expression rapidly is understood to mean after the first 3 to 5 passages in general. A mixture of nucleosides may also be added, this mixture being prepared as described above (Pain et al., 1996). Among the basal media tested under these same conditions and which give similar results are the HamF12, Glasgow MEM and DMEM media, the latter supplemented with biotin at a final concentration of 8 mg/l. By way of comparison, the biotin concentration is 0.2 mg/l in the MacCoy medium, 0.0073 mg/l in the HamF12 and 0 in the commercial DMEM and GMEM media.

The growth factors and the cytokines added to the culture medium are preferably factors and cytokines which are recombinant, including mouse SCF at a final concentration of 1 ng/ml, IGF-1 at a final concentration of 1 to 5 ng/ml, CNTF at a final concentration of 1 ng/ml, IL-6 at a final concentration of 1 ng/ml, and the soluble IL-6 receptor at a final concentration of 0.5 ng/ml to 1 ng/ml. In some experiments, some other factors may be added during the first passages. For example up to passage 3 or 10, it is possible to add bFGF to the medium at a final concentration of 1 ng/ml and IL-11 at a final concentration of 1 ng/ml.

The inoculation is carried out into this medium on the inactivated "feeder" composed of mouse fibroblasts established as lines, the STO cells. In some cases, these cells were transfected with simple expression vectors allowing the expression of growth factors such as avian SCF, constitutively in the STO cells. Thus, this "feeder" produces the factor in a form which is soluble and/or attached in the plasma membrane of the cells.

After initial inoculation of the cells directly into this medium, the medium is partially changed the next day, and then partially or completely during subsequent days, depending on the rate of adhesion observed for the primary cells. After about 4 to 7 days depending on the cases, the initial culture is dissociated and transferred into new dishes in the same initial medium on the inactivated feeder. After three to five passages, the cells are cultured on an inactivated feeder of STO cells which are nontransfected or transfected with an expression vector encoding a resistance to an antibiotic such as the gene for resistance to neomycin, to hygromycin, to puromycin and the like. After about twenty passages, the cells are progressively deprived of growth factors and cytokines. The expression gradual withdrawal is understood to mean a removal factor by factor from the culture medium. Thus, at one passage, SCF is first of all removed, and then, two or three passages later, IGF-1. If the cells do not exhibit morphological alterations or a variation in their average rate of proliferation, the other factors, such as CNTF and IL-6, are then removed. This withdrawal may also be drastic. All the factors are in this case removed all at once. The cells are then observed and are only passaged several days later if their rate of proliferation is modified. The latter solution is generally that which is practiced.

Various isolates are thus obtained and maintained for very long periods of time. The expression very long periods of time is understood to mean periods of the order of several weeks with a minimum of 50 days, preferably periods greater than 200 to 400 days, without limitation in time. Periods greater than 600 days are observed.

Regardless of the support used, all the cells which are adherent are dissociated with a proteolytic dissociation enzyme, such as pronase, collagenase, dispase, trypsin, and the like. Preferably, a proteolytic enzyme of bacterial origin is used in order to avoid any potential contaminant of animal origin.

These cells have the characteristics of embryonic stem cells with a specific morphology illustrated, by way of example, by the photograph of FIG. 4 i.e. a small size, a large nucleocytoplasmic ratio, a nucleus with at least one nucleolus which is clearly visible and a very small cytoplasm. These cells are characterized by growth in the form of more or less compact solid masses. The adherent and nonadherent cells exhibit cross-reactivity with a number of antibodies, as described above in Pain et al., 1996 and in U.S. Pat. No. 6,114,168 and EP 787 180. The endogenous telomerase activity component is also present and is an important factor in the "stem" nature of these cells.

Cells of different isolates are obtained and maintained for long periods of time.

Table 1 illustrates a few of the characteristics of these isolates

| Name | Species | Start | "Stoppage" | Days | Passage | Generation |
|---|---|---|---|---|---|---|
| S86N16 | Chicken S86N | 26 Jan. 2000 | 05 Aug. 2001 | 559 | 207 | 692 |
| WL3 | Chicken WL | 28 Jun. 2000 | 09 Aug. 2001 | 403 | 153 | 333 |
| Valo4 | Chicken Valo | 26 Sep. 2000 | 07 Feb. 2002 | 401 | 135 | 317 |
| S86N45 | Chicken S86N | 29 Jan. 2001 | 12 Nov. 2001 | 287 | 118 | 329 |

It will be noted that the term "stoppage" does not correspond to the end of the proliferation of the cells but to a deliberate stoppage of the cell cultures by the experimenter. The number of generation n is obtained by the formula $X=2^n$ or X is the theoretical cumulative number of cells. This number is available since the cells are counted at each passage and during each inoculation. The complete history of the culture is thus available.

EXAMPLE 3

Passage of the Cells

One of the characteristics of stem cells, in particular somatic stem cells and embryonic stem cells, is their capacity to proliferate in vitro for considerable periods of time. In order to propagate and to passage the cells, the culture medium is changed and replaced with fresh medium a few hours before their passage. The curve presented in FIG. 1 illustrates a profile of cell growth and establishment.

EXAMPLE 4

Doubling Time and Average Division Time

Starting with the established cells in culture and the cells presented in the preceding examples, a mean division time can be calculated. For all the independent isolates obtained, the rate of proliferation increases slightly during successive passages, thus causing the average division time during the establishment of the cells to vary. In the adherent phase, the cells are initially inoculated on an inactivated feeder layer and are passaged regularly at a constant initial inoculation density of 1 to $2 \times 10^6$ cells per 100 mm dish. Table 2 illustrates the doubling time (d) and the mean division time (MDT in hour) for 3 established cell types as a function of the culture time. It is observed that the mean doubling time decreases during the establishment.

TABLE 2

| Cells | days | | | | | | | | | | |
|---|---|---|---|---|---|---|---|---|---|---|---|
| | 50 | 100 | 150 | 200 | 250 | 300 | 350 | 400 | 450 | 500 | 550 |
| S86N16 (d) | 0.30 | 0.63 | 1.00 | 0.86 | 1.13 | 1.15 | 1.47 | 1.70 | 1.94 | 1.50 | 1.9 |
| S86N16 (MDT) | 80 | 38 | 24 | 27.9 | 21.2 | 20.9 | 16.3 | 14.1 | 12.4 | 16 | 12.6 |
| S86N45 (d) | 0.49 | 0.89 | 0.89 | 1.45 | 2.15 | x | x | x | x | x | x |
| S86N45 (MDT) | 49 | 26.8 | 27 | 16.5 | 11.1 | x | x | x | x | x | x |
| Valo4 (d) | 0.03 | 0.61 | 1.00 | 1.17 | 1.26 | 1.03* | 1.08* | 1.25* | x | x | x |
| Valo4 (MDT) | >48 | 39.3 | 24 | 20.5 | 19 | 23.3 | 22.2 | 19.2 | x | x | x |

The mean doubling time d is established for the period of time indicated in days with the following formula: d = (1/Log2 × (LogX2/X1)) × 1/(T2 − T1) where X2 and X1 are total numbers of cells at the times T2 and T1. This formula is the direct consequence of the calculation of the number of generations N by the formula $X = 2^n$ presented in example 1. The mean division time (MDT) is then obtained in hours by dividing 24 hours by d.
*The Valo cells are passaged during this establishment on a plastic support without the presence of a feeder. The doubling time decreases and then increases again, when the cells become rehabituated to this new environment.

EXAMPLE 5

Control of the Level of Serum for the Proliferation of the Lines

During the obtaining of these lines, the culture media used are conventional culture media comprising a base (DMEM, GMEM, HamF12, McCoy, and the like) supplemented with various additives such as nonessential amino acids, vitamins, and sodium pyruvate. This complex medium comprises fetal calf serum, which remains a central component of the culture, even though components of different origins, including plant components, can be gradually used. A process for controlling and habituating the cells to relatively low proportions of fetal calf serum is presented. It is thus possible to maintain cells in high proliferation (division time>1) with low percentages of serum (2% for example in the case of the S86N16 cells).

The curves presented in FIG. 2 illustrates the relative reduction of serum for a given cell type: S86N16 cells. The doubling time and the mean division times were also calculated and presented in table 3. It will be noted that the mean division time increases as a function of the relative reduction in serum. A recovery phase is nevertheless observed after some time in culture under the conditions mentioned. This time remains nevertheless less than 24 h (d>1), which already represents a very advantageous proliferation in industrial terms even at serum concentrations of 2%, which is already relatively low. Improvements with regard to the different metabolites to be used may be envisaged in order to increase this time and still further optimize the culture conditions.

TABLE 3

| Condition | 10% | 7.5% | 3.75% | 2% |
|---|---|---|---|---|
| d | 2.02 | 1.51 | 1.47 | 1.08 |
| MDT | 11.9 | 15.8 | 16.3 | 22.2 |

The examples are taken between passages p204 and p179 for the 10% condition, between p198 and p176 for the 7.5%, between p224 and p201 for the 3.75% and between p216 and p199 for the 2%.

EXAMPLE 6

Deprivation of the Cells of Feeder Layer

Under the initial culture conditions, the presence of a layer of inactivated cells appears to be necessary in order to obtain embryonic stem cells as was described above. This feeder layer no longer appears to be necessary after a number of passages. Only the "culture treated" plastic appears to be important. Indeed, one of the characteristics of some eukaryotic cells is to proliferate in adherent form. In order to facilitate the adhesion of the cells, the various plastic materials used are "culture" treated. They undergo during their manufacture a treatment which adds charges at the surface of the plastic, which charges promote the adhesions of the extracellular matrix of the cells. By contrast, the cell culture untreated plastic, often called plastic of bacteriological quality, is not surface treated by addition of specific feeders. The adhesion of the cells thereto is generally very difficult, or even impossible, or then induces changes in morphology, and in behavior which are often drastic. This distinction between the two plastic qualities makes it possible to obtain, depending on the inoculations which are carried out therein, cells with different behaviors. Gradual deprivation of the cultures of inactivated "feeder" makes it possible to obtain, after a few passages, homogeneous cultures of stem cells directly inoculated on "culture treated" plastic.

The comparative growth curves for the cells maintained in the presence and in the absence of inactivated "feeder" are presented with the case of the S86N16 cells in FIG. 3. This adaptation of the cells is progressive so as not to lose the stem cell character of the cells initially maintained on a "feeder". Progressive derivatives are thus made. The obtaining of cells which proliferate on plastic is the accomplishment of the withdrawal process. In table 4, the division times show sensitivity of the cells to their environment. As in the case of the progressive withdrawal of serum, an adaptation is obtained with a recovering effect on the cells after a few passages under the conditions defined.

TABLE 4

| Condition | 1.2 | 0.5 | 0.3 | plastic |
|---|---|---|---|---|
| d | 1.95 | 1.84 | 1.39 | 1.42 |
| MDT | 12.3 | 13 | 17.3 | 16.9 |

The examples are taken between the passages p154 and p131 for the 3 conditions $1.2 \times 10^6$, $0.5 \times 10^6$ and $0.3 \times 10^6$ feeder cells and between p161 and p139 for the condition on plastic alone.

EXAMPLE 7

Deprivation of the Cells in Growth Factors

Under the initial culture conditions, the presence of growth factors is necessary. It is possible to schematically distinguish two families of factors: the cytokines and the trophic factors.

The cytokines are mainly cytokines whose action is through a receptor which is associated with the gp130 protein. Thus, LIF, interleukin 11, interleukin 6, CNTF, oncostatin and cardiotrophin have a similar mode of action with the recruitment at the level of the receptor of a specific chain and the combination of the latter with the gp130 protein in monomeric or sometimes heterodimeric form. In a few cases, the combination of a soluble form of the receptors, a form described inter alia for the receptors for interleukin 6 and CNTF, makes it possible to increase the proliferative effect observed. It has been previously shown that the addition of at least one of these cytokines appeared to be necessary for obtaining embryonic stem cells.

The trophic factors are mainly SCF, IGF-1 and bFGF, which are also used at the start of the Culture, as described above. Their presence is also necessary for obtaining and amplifying the cells.

By progressively reducing these growth factors, it is possible to obtain, after a few passages, culture conditions which allow the proliferation of the embryonic or somatic stem cells without the addition of an exogenous growth factor. The different markers used to characterize these cells are always positive for the cells maintained with no factors.

EXAMPLE 8

Comparison of the Media Used

Inoculated into different media, the cells are not obtained with the same frequencies. Comparison of the compositions of the media makes the identification of one of the components in particular difficult. It appears more likely that the whole combination allows an improvement in the physiology of the cells. Among the preferred media, the Ham F12 medium, the MacCoy medium, the DMEM medium and a DMEM medium enriched with biotin will be noted. Starting with such an isolate, adaptation trials are carried out in these different media.

EXAMPLE 9

Establishment of the Nonadherent Cells

During the successive passages of the stem cells, a high-density inoculation directly into the bacteriological dish makes it possible to obtain, after a few passages, embryonic cells which become detached from their substrate and which proliferate in suspension in the form of small regular aggregates. This proliferation is encouraged over several passages by mere dilution, mechanical dissociation and nonuse of proteolytic enzyme. The stirring of the cultures is generally carried out but does not represent a distinguishing factor for obtaining nonadherent cells. Like the adherent cells, these cells have a characteristic morphology of stem cells, i.e. a small size, a large nucleocytoplasmic ratio, a nucleus with at least one nucleolus which is clearly visible and a very small cytoplasm. These cells are characterized by a growth in small aggregates which are more or less compact. These nonadherent cells exhibit cross-reactivity with a number of antibodies, as described above in Pain et al., 1996. These cells are also positive for the endogenous telomerase activity (as presented in example 10 for the EB1, EB4 and EB5 cells). In a nonadherent phase, the cells exhibit a high proliferation in different media. The initial inoculation density and the very regular supply of fresh medium provides high densities which may range above $1 \times 10^6$ cells per ml. Table 5 summarizes the main characteristics of a few isolates (parental cells, initial passage of the making into a suspension, number of days maintained in culture in suspension, number of passages and of generations obtained before voluntary stoppage of the maintenances). It can thus be noted that the passage for the making into a suspension can vary from one isolate to another (see isolate EB1 and EB14) and the proliferation rate (see isolate EB3 and EB14).

TABLE 5

| Name | Parental cells | Initial passage | Start | Days | Passages | Generations |
|---|---|---|---|---|---|---|
| EB1 | S86N16 | p111 | 20 Jan. 2001 | 184 | 41 | 120 |
| EB3 | S86N16 | p118 | 23 Jan. 2001 | 381 | 17 | 40 |
| EB4 | S86N45 | p100 | 25 Sep. 2001 | 44 | 17 | 40 |
| EB5 | S86N45 | p100 | 25 Sep. 2001 | 44 | 17 | 40 |
| EB14 | S86N45 | p81 | 05 Sep. 2002 | 70 | 24 | 65 |

It will be noted that the term "start" corresponds to the cells being placed under nonadherence.

EXAMPLE 10

Characterization of the Established Cells

The stem cells maintained for long culture times are characterized with the same criteria as those described above (Pain et al., 1996). It is thus possible to regularly detect the endogenous alkaline phosphatase activity, illustrated by the photograph of FIG. 5, the endogenous telomerase activity and reactivity with specific antibodies such as the antibodies SSEA-1 (TEC-01) and EMA-1.

One of the important criteria during the establishment of the cells is the presence of telomerase. Various tests were carried out during the maintenance of the cells in culture using a TRAP detection kit (Telomerase PCR Elisa, Roche). The cells are detected positive after various passages in culture. Thus, the telomerase activity is detectable for the S86N16 cells, the S86N45 cells and for the EB1, EB4 and EB5 cells which are derived therefrom in a nonadherent form (see table 6). The CEFs (Chicken Embryonic Fibroblasts) maintained in primary culture are considered as negative. The threshold of an OD<0.2 is the threshold recommended by the kit as the negative threshold. All the analyses were carried out on an equivalent of 2000 cells.

TABLE 6

Assay of the telomerase activity in various lines at various passages

| Cells | Passage | Telomerase OD |
|---|---|---|
| S86N16 | p12 | 1.7 |
|  | p29 | 2.8 |
|  | p185 | 0.97 |
|  | p204 | 0.95 |
| S86N16 EB1 | p134 | 1.1 |
| S86N45 | p50 | 0.87 |
|  | p58 | 1.1 |
|  | p66 | 0.96 |
|  | p94 | 1.2 |
| S86N45 EB4 | p112 | 1.4 |
| S86N45 EB5 | p112 | 0.94 |
| CEF* | p4 | 0.07 |

EXAMPLE 11

Transfection and Induction of the Cells

The stem cells maintained in a growth over the long term are transfected with various expression plasmids. It has been shown that avian stem cells could be transfected (Pain et al., 1996). In particular, the nonadherent cells are transfected and various sorting systems make it possible to identify the stably transfected cells (cell sorting, limiting dilution, and the like). These genetic modifications can be made at the undifferentiated stage of the stem cell. Once this modification has been obtained, the cell is then induced to differentiate spontaneously or by addition of a differentiation inducer. In this case, it is possible to use retinoic acid at concentrations of $10^{-8}$ M to $10^{-6}$ M, or dimethyl sulfoxide at concentrations of 1 to 2% final or sodium butyrate at concentrations of $10^{-4}$ to $10^{-8}$ M, or phorbol ester (TPA, PMA, and the like) or lipopolysaccharides (LPS) at concentrations of 1 to 5 µg/ml final. In another example, the cells can form embryoid bodies in suspension, which embryoid bodies can be caused to adhere to plastic after dissociation or nondissociation of the cells constituting them. These differentiated cells then proliferate but have a more limited capacity for proliferation over the long term. By targeting the genetic modification on a gene which influences the proliferation of the cells, it is possible to make these differentiated cells capable of proliferating over the long term.

EXAMPLE 12

Infection of the Cells

The adherent and nonadherent cells can be infected with different viruses and retroviruses including avian viruses and retroviruses. These cells can thus serve as a replication support for the production of viral stocks intended for the production of live, attenuated or inactivated human and veterinary vaccines depending on the cases. Among the viruses of interest, there may be mentioned those of the family of adenoviruses (such as Human Adenovirus C, Fowl Adenovirus A, Ovine Adenovirus D, Turkey Adenovirus B), circoviridae (such as Chicken Anemia Virus, CAV), certain coronaviruses, such as avian infectious bronchitis virus (IBV), flaviviruses (such as Yellow fever virus and hepatitis C virus), hepadnaviruses (such as Hepatitis B virus and Avihepadnaviruses such as Duck hepatitis B virus); herpesviruses (such as Gallid herpesvirus, HSV (Herpes simplex virus) and Human herpesvirus 1, 3 and 5), orthomyxoviruses (such as the influenza virus: Influenzavirus A, Influenzavirus B and Influenza-virus C), papovaviruses (such as polyomavirus and more particularly Simian virus 40), paramyxoviruses (such as measles, mumps and rubella viruses and such as respiroviruses and pneumoviruses such as human respiratory syncytial virus and Metapneumovirus such as Avian pneumovirus), picornaviruses (such as polio virus, hepatitis A virus, and such as Encephalomyocarditis virus and foot-and-mouth disease virus), poxviruses (such as fowlpox virus and avipox viruses including Canarypox viruses, Juncopox viruses, Mynahpox viruses, Pigeonpox viruses, Psittacinepox viruses, Quailpox viruses, Sparrowpox viruses, Starlingpox viruses, Turkeypox viruses), orthopoxvirus such as vaccinia virus, MVA, and reoviruses (such as rotaviruses), retroviruses (such as ALV, avian leukosis virus, Gammaretroviruses such as Murine leukemia virus, Lentiviruses such as Human immunodeficiency virus 1 and 2) and Togaviridae such as Rubivirus, in particular Rubella virus.

EXAMPLE 13

Protocol for Infecting a Nonadherent Avian Cell Line (EB1) with a Virus

Amplification of the Cells:
The EB1 or EB14 cells are inoculated into a medium, preferably MacCoy's 5A, HAMF12 or DMEM medium, or any other medium of interest, containing 5% serum at a concentration of $0.2 \times 10^6$ cells/ml for an initial volume of 50 ml in general. They are maintained in culture at 39° C. and at 7.5% $CO_2$, with stirring. Fresh medium is added every day for the 3 to 4 days for which the amplification lasts in order to reach a cell concentration of 1 to $3 \times 10^6$ cells/ml for a final culture volume of 100 to 250 ml.

The cells in suspension are collected and centrifuged for 10 min at 1 000 rpm approximately. The pellet is resuspended in 20 to 50 ml of 1×PBS (Phosphate buffer Salt). The cells are then counted, centrifuged and the pelleted cells are taken up in a serum-free medium at a final concentration of 3 to $5 \times 10^6$ cells/ml. Several tubes are then prepared under these conditions containing 3 to $5 \times 10^6$ cells per tube.

Preparation of the Virus and Infection:
The viral stock having a known titer is rapidly thawed at 37° C. and diluted in serum-free medium at a titer of 10× to 1 000× the concentration necessary for the final infection. The cells are infected with the virus of interest at an m.o.i. (multiplicity of infection) of 0.01 to 0.5 according to the types of virus, which involves adding between 0.1 and 10% volume/volume of viral suspension to the cellular pellet. After incubating for 1 hour at an optimum temperature for the virus, in general from 33 to 37° C., the cells are again centrifuged and the medium removed with care. This step is found to be often necessary in order to limit the effect of the initial virus in the subsequent process. One of the possibilities is to directly dilute the cells without centrifuging them again with serum-containing medium (5% of serum) at a final concentration of 0.2 to $1 \times 10^6$ cells/ml and incubated again.

Harvesting of the Supernatant and of the Cells:
After 2 to 4 days of incubation, depending on the viral kinetics and the potential cytopathic effect of certain viruses, the medium containing the cells or the cellular debris is harvested. Depending on the viruses, only the pellet or the supernatant may be of interest and contain the viral particles. The cells are harvested and centrifuged. The collected supernatant is centrifuged again for 5 to 10 minutes at 2 500 rpm, and stored at −80° C. before purification of the particles. An aliquot is collected in order to carry out the titration. The cellular pellet is taken up in 5 ml of serum-free medium, sonicated and centrifuged for 5 to 10 minutes at 2 500 rpm. The supernatant obtained is stored at −80° C. up to the purification and the titration of an aliquot.

The viral infection and production efficiencies are compared between the various conditions performed. For the viruses with cytopathic effects, the titrations are in general carried out by the lysis plaque technique.

EXAMPLE 14

Protocol for Infecting an Adherent Avian Cell Line (S86N45) with a Virus

Preparation of the Cells:
The cells are inoculated 48 hours before the infection into T150 flasks at a concentration of between 0.03 and $0.06 \times 10^6$ cells/cm$^2$ in a medium, preferably MacCoy's 5A, HAMF12 or DMEM medium, or any other medium of interest, containing 5% serum. They are maintained at 39° C. and 7.5% $CO_2$.

Infection:
The viral stock having a known titer is rapidly thawed at 37° C. and diluted in serum-free medium at a titer of 10× to 1 000× the concentration necessary for the final infection. The cells are infected with the virus of interest at an m.o.i. (multiplicity of infection) of 0.01 to 0.5 according to the types of virus, which involves adding between 0.1 and 10% volume/volume of viral suspension to the cellular pellet. The infection is generally carried out in a minimum of medium (from 5 to 10 ml for a 75 cm$^2$ flask) in a medium containing 0% serum.

After incubating for 1 hour at the optimum temperature for the virus, in general from 33 to 37° C., 20 ml of medium 5% are added to the flasks. In a particular case, the cells can be washed with PBS in order to remove the particles which might be attached to the cells. In the case of a cytopathic virus, the cells are observed daily after the infection in order to monitor the appearance of the cell lysis plaque, which indicates good progress of the infection.

Harvesting of the Supernatant and of the Cells:

After 2 to 4 days of incubation, depending on the viral kinetics and the potential cytopathic effect of certain viruses, the medium containing the supernatant, the cells and the cellular debris are harvested. Depending on the viruses, only the pellet or the supernatant may be of interest and contain the viral particles. The cells are harvested and centrifuged. The collected supernatant is centrifuged again for 5 to 10 minutes at 2 500 rpm, and stored at −80° C. before purification of the particles. An aliquot is collected in order to carry out the titration. The cellular pellet is taken up in 5 ml of serum-free medium, sonicated and centrifuged for 5 to 10 minutes at 2 500 rpm. The supernatant obtained is stored at −80° C. up to the purification and the titration of an aliquot.

The viral infection and production efficiencies are compared between the various conditions performed. For the viruses with cytopathic effect, the titrations are in general carried out by the lysis plaque technique.

EXAMPLE 15

Replication of a Recombinant Avipox on Nonadherent Avian Stem Cells of the EB1 Line The nonadherent stem cells EB1 at passage 138 are amplified and then infected at an m.o.i. of 0.1 with a recombinant avipox producing a protein of interest. After the infection, the cells are maintained in a spinner for the 4 days for which the infection lasts. An aliquot is removed from the second day and then the next two days in order to monitor the variation of the viral titer both in the supernatant and in the intracellular content, after lysis of the cellular content. The titration is carried out by the lysis plaque technique.

Table 7 illustrates the results obtained. These results demonstrate the very satisfactory replication of the recombinant avipox on the EB1 stem cells. Thus, the infectious titer progresses throughout the culture and the course of the infection, reaching a maximum of 7.2 PFU/cell (PFU: Plating Forming Unit) after 4 days of incubation. This titer is at least equivalent to that obtained for this same recombinant avipox on primary chicken embryo cells.

This titer can be improved by specific culture conditions and optimization procedures.

It will also be noted that at least equivalent infectious titers were also obtained on a larger scale in 3 liter bioreactors.

TABLE 7

Kinetics of titration of the recombinant avipox on nonadherent EB1 stem cells

| Sampling (h after infection) | 50 hours | 74 hours | 97 hours |
|---|---|---|---|
| Cellular fraction (Log PFU/ml) | 6.40 | 6.37 | 5.99 |
| Supernatant (Log PFU/ml) | 5.56 | 5.8 | 6.29 |
| Total (Log PFU/ml) | 5.78 | 5.94 | 6.31 |
| PFU/cell | 2.2 | 3.2 | 7.2 |

EXAMPLE 16

Replication of Modified Vaccinia Virus Ankara (MVA) on Adherent and Nonadherent Avian Stem Cells of the S86N45 Line and EB14 Line The MVA virus (titer $2.5 \times 10^7$ TCID50/ml in 0.5 ml vials) was received under frozen conditions.

For safety reasons, the MVA virus and infected cells were kept under controlled conditions (−80° C. freezer) and the contaminated plastic material was placed into hypochloride solution for more than 1 hour and then place into a bag for full and complete autoclave inactivation.

Experiments and Results

The S86N45 and EB14 cells were thawed in a HamF12 based complete medium.

The adherent S86N45 cells were amplified quite rapidly, with a good growth rate and a nice morphology.

The cells were infected 1 hour in 2 ml of PBS with the different m.o.i. of interest with no washing with PBS after the infection. The medium was just added to the complete infectious medium, i.e. the added virus was not removed.

After 3 days of infection, the cell lysis appears to be proportional to the used m.o.i. This cytopathic effect is a good indicator of the virus infection of the cells. So cells and supernatant are harvested and stored at −80° C. before purification of particles and/or titration.

The non adherent EB14 cells were amplified. The cells were infected, not washed, and the complete medium directly added on the inocculum after 1 hour of contact with viral particles. After 3 days, a characteristic cell lysis was observed. The non infected cells used as the control were counted and a good growth was demonstrated, showing good culture conditions and therefore confirming an efficient lysis by the virus in the infected culture. Cells and supernatant are harvested and stored at −80° C. before purification of particles and/or titration (see table 8).

TABLE 8

Results of the titration

| Cell Type | M.O.I. | Trial | Virus/ pellet of 10E6 cells | Titer/mL based on 14 ml total volume | Virus yield/ cell | Average virus yield/ cell |
|---|---|---|---|---|---|---|
| S86N45 | 0 | 1 | 0 | 0 | 0 | 0 |
|  | 0 | 2 | 0 | 0 | 0 |  |
|  | 0.1 | 1 | $1-3 \times 10^7$ | $\geq 6 \times 10^5$ | 5-15 | 5-15 |
|  | 0.1 | 2 | $1-3 \times 10^6$ | $1-3 \times 10^5$ | 1-5 |  |
|  | 0.01 | 1 | $1-3 \times 10^7$ | $1-3 \times 10^6$ | 15-30 | $\geq 30$ |
|  | 0.01 | 2 | $4-6 \times 10^7$ | $1-3 \times 10^6$ | $\geq 30$ |  |
| EB14 | 0 | 1 | 0 | 0 | 0 | 0 |
|  | 0.1 | 1 | $1-3 \times 10^7$ | $1-3 \times 10^6$ | 15-30 | 15-30 |
|  | 0.1 | 2 | $1-3 \times 10^7$ | $1-3 \times 10^6$ | 15-30 |  |
|  | 0.05 | 1 | $\geq 6 \times 10^7$ | $4-6 \times 10^6$ | $\geq 50$ | $\geq 50$ |
|  | 0.05 | 2 | $1-3 \times 10^7$ | $1-3 \times 10^6$ | 15-30 |  |
|  | 0.01 | 1 | $1-3 \times 10^7$ | $1-3 \times 10^6$ | 15-30 | 15-30 |
|  | 0.01 | 2 | $1-3 \times 10^7$ | $1-3 \times 10^6$ | 15-30 |  |

Applicants hereby incorporate by reference PCT/FR03/00735 filed on Mar. 7, 2003, and French application serial no. 0202945 filed Mar. 8, 2002, and all references cited herein.

REFERENCES

Baba T W, Humphries E I L (1985). Formation of a transformed follicle is necessary but not sufficient for development of an avian leukosis virus-induced lymphoma. Proc. Natl. Acad. Sci. USA 82: 213-216.

Beug H, von Kirchbach A, Doderlein G, Conscience J F, Graf T. (1979). Chicken hematopoietic cells transformed by seven strains of defective avian leukemia viruses display three distinct phenotypes of differentiation. Cell 18: 375-390.

Guilhot C, Benchaibi M, Flechon J E, Samarut J. (1993). The 12S adenoviral E1A protein immortalizes avian cells and interacts with the avian RB product. Oncogene 8: 619-624

Kawaguchi T, Nomura K, Hirayama Y, Kitagawa T. (1987). Establishment and characterization of a chicken hepatocellular carcinoma cell line, LMH. Cancer Res 1987 47: 4460-4464.

Kim H, You S, Farris J. Foster L K, Foster D N. (2001). Post-transcriptional inactivation of p53 in immortalized chicken embryo fibroblast cells. Oncogene 20: 3306-3310.

Kim H, You S, Kim I J, Foster L K, Farris J, Ambady S, Ponce de Leon F A, Foster D N. (2001). Alterations in p53 and E2F-1 function common to immortalized chicken embryo fibroblasts. Oncogene 20: 2671-2682.

Liu J L, Klein P A, Moscovici M G, Moscovici C. (1992). Monoclonal antibodies recognizing normal and retrovirus-transformed chicken hematopoietic cells. Virology 189: 583-591.

Moscovici C, Moscovici M G, Jimenez H, Lai M M, Hayman M J, Vogt P K. (1977). Continuous tissue culture cell lines derived from chemically induced tumors of Japanese quail. Cell 11: 95-103.

Pain B., Clark M. E., Shen M., Nakazawa H., Sakurai M., Samarut J., Etches R J. (1996). Long-term in vitro culture and characterisation of avian embryonic stem cells with multiple morphogenetic potentialities. Development 122: 2339-2348.

Pain B., Chenevier P., Samarut J. (1999). Chicken embryonic stem cells and transgenic strategies. Cells Tissues Organs 165: 212-219.

Samarut J, Gazzolo L. (1982). Target cells infected by avian erythroblastosis virus differentiate and become transformed. Cell 28: 921-929.

Smith J R and Pereira-Smith O M (1996). Replicative senescence: implications for in vivo aging and tumor suppression. Science 273, 63-67.

The invention claimed is:

1. A method for establishing an avian cell line, said method comprising:
   (a) isolating cells from a blastodermal disk of a fertilized avian egg;
   (b) culturing said isolated cells in a basal culture medium supplemented with
      i) mouse stem cell factor (SCF), insulin-like growth factor 1 (IGF-1), ciliary neurotrophic factor (CNTF), interleukin 6 (IL-6), soluble IL-6 receptor (sIL-6r), and basic fibroblast growth factor (bFGF), and optionally interleukin 11 (IL-11);
      (ii) a layer of feeder cells; and
      (iii) animal serum;
   (c) culturing said cells of step (b) in basal culture medium comprising IGF-1 and CNTF as the only supplemental growth factors and cytokines, a layer of feeder cells, and animal serum such that an avian cell line capable of being infected by and replicating viruses is obtained.

2. The method of claim 1, wherein the avian cell line is capable of being cultured in the absence of said trophic factors and cytokines for at least 50 days.

3. The method of claim 1, wherein the avian cell line is nonadherent.

4. The method of claim 1, wherein the avian cell line exhibits alkaline phosphatase (AP) activity and reacts with antibodies that bind to SSEA-1, SSEA-3, or EMA-1.

5. The method of claim 1, wherein said basal medium is selected from the group consisting of DMEM medium, GMEM medium, HamF12 medium, and McCoy, and wherein said basal medium is supplemented with additives selected from the group consisting of nonessential amino acids, vitamins, and sodium pyruvate.

6. The method of claim 1, wherein said avian egg is a chicken egg.

7. The method of claim 1, wherein the basal medium is selected from the group consisting of DMEM medium, GMEM medium, HamF12 medium, and MacCoy medium.

8. The method of claim 1, further comprising culturing the avian cell line obtained in step (d) in reduced amounts of said STO cells up to the absence of said STO cells.

9. The method of claim 1, wherein said cells of step (c) are cultured in a basal medium free of one or more of said trophic factors and cytokines.

10. The method of claim 1, wherein said avian cell line exhibits alkaline phosphatase (AP) or telomerase activity, or
reacts with antibodies that bind to SSEA-1, SSEA-3, or EMA-1.

* * * * *